US010479817B2

(12) United States Patent
Rosi et al.

(10) Patent No.: US 10,479,817 B2
(45) Date of Patent: Nov. 19, 2019

(54) TEMPLATES FOR CONTROLLING SYNTHESIS OF NANOPARTICLES INTO DISCRETE ASSEMBLIES

(71) Applicant: University of Pittsburgh—Of the Commonwealth System of Higher Education, Pittsburgh, PA (US)

(72) Inventors: Nathaniel L. Rosi, Pittsburgh, PA (US); Chun-Long Chen, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 381 days.

(21) Appl. No.: 14/931,805

(22) Filed: Nov. 3, 2015

(65) Prior Publication Data

US 2016/0052969 A1 Feb. 25, 2016

Related U.S. Application Data

(62) Division of application No. 12/211,668, filed on Sep. 16, 2008, now Pat. No. 9,206,233.

(60) Provisional application No. 60/981,137, filed on Oct. 19, 2007.

(51) Int. Cl.
| | | |
|---|---|---|
| *C07K 7/08* | (2006.01) | |
| *B22F 1/00* | (2006.01) | |
| *B82Y 30/00* | (2011.01) | |
| *C07K 7/06* | (2006.01) | |
| *C22B 3/00* | (2006.01) | |

(52) U.S. Cl.
CPC .............. *C07K 7/08* (2013.01); *B22F 1/0018* (2013.01); *B82Y 30/00* (2013.01); *C07K 7/06* (2013.01); *B22F 2001/0033* (2013.01); *B22F 2998/00* (2013.01); *C22B 11/04* (2013.01)

(58) Field of Classification Search
None
See application file for complete search history.

(56) References Cited

U.S. PATENT DOCUMENTS

| | | | |
|---|---|---|---|
| 5,145,684 | A | 9/1992 | Liversidge et al. |
| 2004/0033345 | A1 | 2/2004 | Dubertret et al. |
| 2005/0064508 | A1 | 3/2005 | Belcher et al. |
| 2005/0130258 | A1* | 6/2005 | Trent et al. ................ 435/68.1 |
| 2005/0196870 | A1 | 9/2005 | Sun |
| 2006/0172282 | A1* | 8/2006 | Naik et al. ...................... 435/5 |
| 2008/0220075 | A1 | 9/2008 | Merisko-Liversidge et al. |
| 2009/0261498 | A1 | 10/2009 | Rheinnecker et al. |

OTHER PUBLICATIONS

Slocik et al., Synthesis of Gold Nanoparticles Using Multifunctional Peptides. Small. vol. 1, Issue 11, pp. 1048-1052, Nov. 2005; first published online:Sep. 5, 2005 (http://onlinelibrary.wiley.com/doi/10.1002/smll.200500172/full.*
Shimizu et al. Supramolecular Nanotube Architectures Based on Amphiphilic Molecules. Chem. Rev., 2005, 105 (4), pp. 1401-1444, see esp. p. 1416.*
Sergey E. Paramonov et al., "Self-Assembly of Peptide-Amphiphile Nanofibers: The Roles of Hydrogen Bonding and Amphiphilic Packing", J, Am. Chem. Soc., 2006, 128, 7291-7298. (in Nov. 3, 2015 IDS, #A47).*
Kirsten L. Genson et al., "Langmuir—Blodgett Monolayers of Gold Nanoparticles with Amphiphilic Shells from V-Shaped Binary Polymer Arms", Langmuir 2006, 22, 7011-7015.
Tony Azzam et al., "Monolayer-Protected Gold Nanoparticles by the Self-Assembly of Micellar Poly(ethylene oxide)-b-Poly($\epsilon$-caprolactone) Block Copolymer", Langmuir 2007, 23, 2126-2132.
Eugene R. Zubarev et al., "Amphiphilicity-Driven Organization of Nanoparticles into Discrete Assemblies", J. Am. Chem. Soc., 2006, 128, 15098-15099.
M. M. Tomczak et al., "Bio-based approaches to inorganic material synthesis", Biochemical Society Transactions (2007) vol. 35, part 3, pp. 512-515.
Gul Ahmad et al., "Rapid-Room-Temperature Formation of Crystalline Calcium Molybdate Phosphor Microparticles via Peptide-Induced Precipitation", Adv. Mater. 2006, 18, 1759-1763.
Oana M. Martin et al., "Synthesis and Self-assembly of Amphiphilic Semfluorinated Calix[4]arenas", Supramolecular Chemistry, Jan.-Mar. 2005, vol. 17 (1-2) pp. 9-15.
Rajesh Naik et al., "Biomimetic synthesis and patterning of silver nanoparticles", Nature Materials, vol. 1, Nov. 2002, pp. 169-172.
Sandra R. Whaley et al., "Selection of peptides with semiconductor binding specificity for directed nanocrystal assembly", Nature, vol. 405, Jun. 8, 2000, pp. 665-668.
Stanley Brown, "Metal-recognition by repeating polypeptides", Nature Biotechnology, vol. 15, Mar. 1997, pp. 269-272.
Jeffrey D. Hartgerink et al., "Self-Assembly and Mineralization of Peptide-Amphiphile Nanofibers," Science, Nov. 23, 2001, vol. 294, pp. 1684-1688.
Ho-Wook Jun et al., "Biomimetic self-assembled nanofibers", Soft Matter, 2006, 2, 177-181.
Xiaojun Zhao et al., "Molecular designer self-assembling peptides", Chem. Soc. Rev., 2006, 35, 1105-1110.
Ehud Gazit, "Self-assembled peptide nanostructures: the design of molecular building blocks and their technological utilization", Chem. Soc. Rev., 2007, 36, 1263-1269.
Sylvain Vauthey et al., "Molecular self-assembly of surfactant-like peptides to form nanotubes and nanovesicles", PNAS, Apr. 16, 2002, 2005, vol. 99, No. 81, pp. 5355-5360.
Toshimi Shimizu et al., "Supramolecular Nanotube Architectures Based on Amphiphilic Molecules", Chem. Rev. 105, 1401-1443 (2005).
Chuanbin Mao et al., "Viral assembly of oriented quantum dot nanowires", PNAS, Jun. 10, 2003, vol. 100, No. 12, 6945-6951.
Yohei Yamamoto et al., "Photoconductive Coaxial Nanotubes of Molecularly Connected Electron Donor and Accepted Layers", Science, vol. 314, Dec. 15, 2006, pp. 1761-1764.

(Continued)

*Primary Examiner* — Maury A Audet
(74) *Attorney, Agent, or Firm* — Foley & Lardner LLP

(57) ABSTRACT

An approach to synthesizing and assembling nanoparticles into discrete, size-tunable, pre-designed architectures is realized in a single synthetic/process step.

9 Claims, 4 Drawing Sheets

Specification includes a Sequence Listing.

(56) References Cited

OTHER PUBLICATIONS

Virgil Percec et al., "Self-assembly of amphiphilic dendritic dipeptides into helical pores", Nature, vol. 430, Aug. 12, 2004, pp. 764-768.
Mary J. Sever et al., "Metal-Mediated Cross-Linking in the Generation of a Marine-Mussel Adhesive", Angew. Chem. Int. Ed., 2004, 43, 447-450.
Mary J. Sever et al., "Synthesis of peptides containing DOPA (3,4-dihyroxyphenylalanine)", Tetrahedron 57, (2001) 6139-6146.
Vicente Marchan et al., "Alternative Procedure for the Synthesis of Methionine-Containing Peptide-Oligonucleotide Hybrids", Eur. J. Org. Chem. 2000, 2495-2500.
Dimitry A. Stetsenko et al., "Efficient Conjugation of Peptides to Oligonucleotides by "Native Ligation"", J. Org. Chem. 2000, 65, 4900-4908.
Sergey E. Paramonov et al., "Self-Assembly of Peptide-Amphiphile Nanofibers: The Roles of Hydrogen Bonding and Amphiphilic Packing", J. Am. Chem. Soc., 2006, 128, 7291-7298.
Zhenxin Wang et al., "The Peptide Route to Multifunctional Gold Nanoparticles", Bioconjugate Chem, 2005, 16, 497-500.
Kazunori Matsuura et al., "Artificial Peptide-Nanospheres Self-Assembled from Three-Way Junctions of β-Sheet-Forming Peptides", J. Am. Chem. Soc., 2005, 127, 10148-10149.
He Dong et al., "Self-Assembly of Multidomain Peptides: Balancing Molecular Frustration Controls Conformation and Nanostructure", J. Am. Chem. Soc., 2007, 129, 12468-12472.
Stanley Brown et al., "A Genetic Analysis of Crystal Growth", J. Mol. Biol. (2000), 299, 725-735.
Rajesh R. Naik et al., "Silica-Precipitating Peptides Isolated from a Combinatorial Phage Display Peptide Library", J. Nanosci. Nanotech. 2002, vol. 2, No. 1, pp. 95-100.
Mark A. Schembri et al., "Bioaccumulation of heavy metals by fimbrial designer adhesins", FEMS Microbiology Letters 170 (1999) 363-371.
Kristian Kjærgaard et al., "Sequestration of Zinc Oxide by Fimbrial Designer Chelators", Applied and Environmental Microbiology, Jan. 2000, vol. 66, No. 1, pp. 10-14.
Duncan J. H. Gaskin et al., "Identification of inorganic crystal-specific sequences using phage display combinatorial library of short peptides: A feasibility study", Biotechnology Letters, 22: 1211-1216,.
Stanley Brown, "Engineered iron oxide-adhesion mutants of the *Escherichia coil* phage λ receptor", Proc. Natl. Acad. Sci. USA, vol. 89, pp. 8651-8655, Sep. 1992.
Seung-Wuk Lee et al., "Ordering of Quantum Dots Using Genetically Engineered Viruses", Science, vol. 296, May 3, 2002, pp. 892-895.
L. Brunsveld et al., "Hierarchical formation of helical supramolecular polymers via stacking of hydrogen-bonded pairs in water", PNAS, Apr.16, 2002, vol. 99, No. 8, 4977-4982.
Chen et al.,"A New Peptide-Based Method for the Design and Synthesis of Nanoparticle Superstructures: Construction of Highly Ordered Gold Nanoparticle Double Helices", J.Am. Chem. Soc. 2008, 130, 13555-13557.
Hwang et al., "Size-Controlled Peptide-Directed Synthesis of Hollow Spherical Gold Nanoparticle Superstructures", Small. vol. 7, Issue 14, pp. 1939-1942, 2011.
Hwang et al., "Preparation of 1-D nanoparticle superstructures with tailorable thickness using gold-binding pepetide conjugates", Chem. Commun., 2011, 47, 185-187.
Song et al., "Expeditious Synthesis and Assembly of Sub-100 nm Hollow Spherical Gold Nanoparticle Superstructures", J. Am. Chem. Soc. 2010, 132, 14033-14035.
Song et al., "Peptide-Directed Synthesis and Assembly of Hollow Spherical CoPt Nanoparticle Superstrcutures", Angew. Chem. Int. Ed. 2013, 52, pp. 1-4.

\* cited by examiner

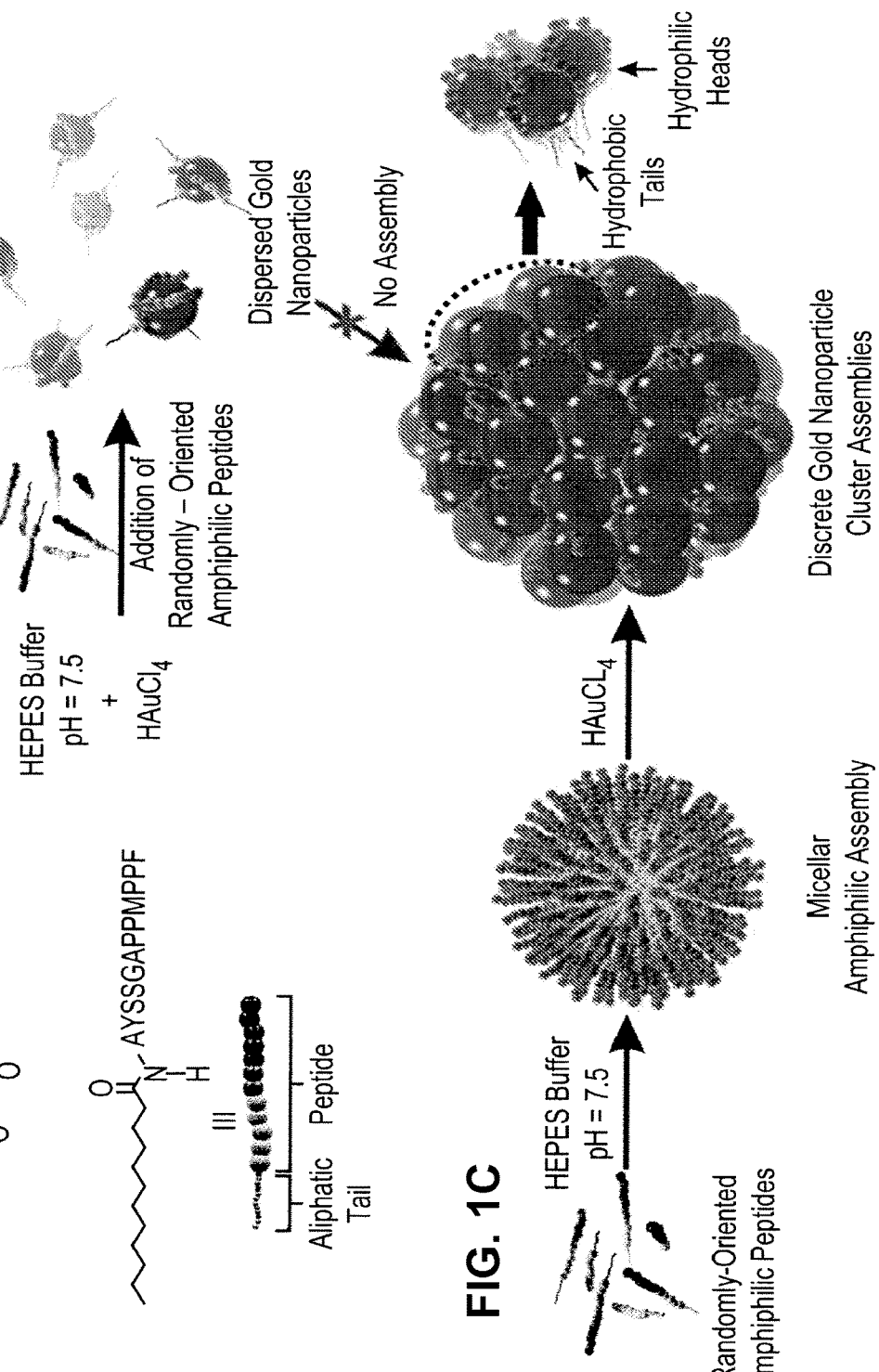

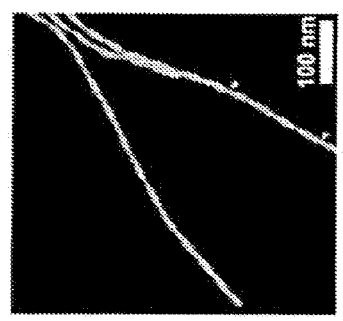
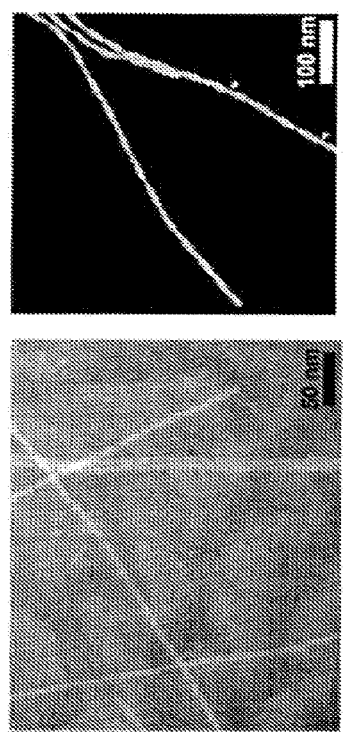
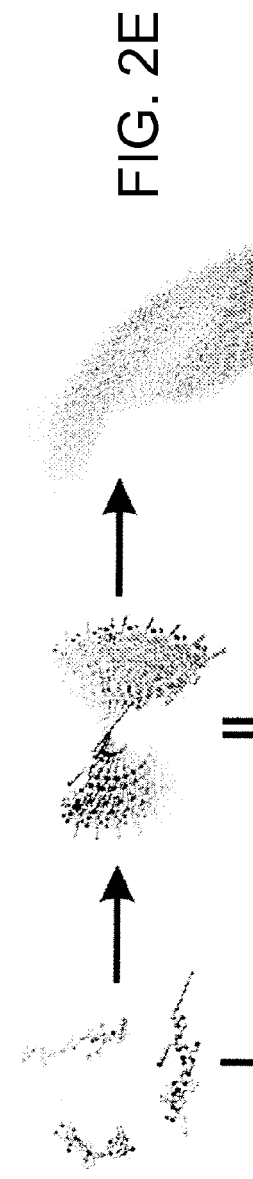
FIG. 2A  FIG. 2B  FIG. 2C  FIG. 2D  FIG. 2E
I: $C_{12}$-$PEP_{Au}$ amphiphiles
II: Assembly of $C_{12}$-$PEP_{Au}$ within nanoribbon
III: Model of $C_{12}$-$PEP_{Au}$-based nanoribbon

SEQUENCE LISTING

```
<160> NUMBER OF SEQ ID NOS: 32

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Tyr Ser Ser Gly Ala Pro Pro Met Pro Pro Phe
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met His Gly Lys Thr Gln Ala Thr Ser Gly Thr Ile Gln Ser
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Lys Thr Ser Leu Gly Gln Ser Gly Ala Ser Leu Gln Gly Ser Glu
1               5                   10                  15

Lys Leu Thr Asn Gly
            20

<210> SEQ ID NO 4
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Gln Ala Thr Ser Glu Lys Leu Val Arg Gly Met Glu Gly Ala Ser Leu
1               5                   10                  15

His Pro Ala Lys Thr
            20

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Thr Ser Thr Trp Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Ser Val Thr Ser Thr Lys
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ser Ser His Leu Asn Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Val Thr Gln Asn Lys Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

```
Ser Pro His Pro Gly Pro Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Ala Pro Thr Pro Met Leu
1               5

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Tyr Ser Ser Gly Ala Pro Pro Met Pro Pro Phe
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Pro Ser Ser Leu Phe Arg Tyr Leu Pro Ser Asp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Leu Ala Thr Gln Pro Pro Arg Thr Pro Pro Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Ser Pro His Pro His Pro Arg His His His Thr
1               5                   10

<210> SEQ ID NO 15
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 15

Arg Gly Arg Arg Arg Arg Leu Ser Cys Arg Leu Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Pro Ser His His His His His Thr Gly Ala Asn
1               5                   10

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Lys Thr Gln Ala Thr Ser Arg Glu Glu Pro Pro Arg Leu Pro Ser
1               5                   10                  15

Lys His Arg Pro Gly
            20

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Asp His Gly Lys Tyr Arg Gln Lys Gln Ala Thr Pro Gly
1               5                   10

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Thr Arg Met Thr Ala Arg Gln His Arg Ser Ala Asn His Lys Ser
1               5                   10                  15

Thr Gln Arg Ala
            20

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 20

Tyr Asp Ser Arg Ser Met Arg Pro His
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

His Thr Gln Asn Met Arg Met Tyr Glu Pro Trp Phe
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asp Val Phe Ser Ser Phe Asn Leu Lys His Met Arg
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Val Arg Pro Lys Ala Ala Thr Asn
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ile Arg His Arg Leu Val Gly Gln
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Arg Thr Val Lys His His Val Asn
1               5

<210> SEQ ID NO 26
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gln Asn Pro Ser Asp Asn Asn Thr His Thr His
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Leu Glu Leu Ala Ile Pro Leu Gln Gly Ser Gly
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Thr Pro Pro Arg Pro Ile Gln Tyr Asn His Thr Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Asn Pro Met His Gln Asn
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Lys Phe Glu Phe Lys Phe Glu
1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Tyr Ser Ser
```

```
<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Pro Pro Met Pro Pro Ala Gly Ser Ser Tyr Ala
1               5                   10
```

TEMPLATES FOR CONTROLLING SYNTHESIS OF NANOPARTICLES INTO DISCRETE ASSEMBLIES

RELATED APPLICATIONS

This application is a divisional of U.S. patent application Ser. No. 12/211,668, filed Sep. 16, 2008, which claims the benefit to priority from U.S. Provisional Patent Application No. 60/981,137, filed Oct. 19, 2007, all of which are incorporated herein by reference in their entirety.

BACKGROUND OF THE INVENTION

Controlling the growth and assembly of nanoparticles is one of the most significant problems facing nanoscience. This is so in part because the size- and shape-dependent physicochemical and optoelectronic properties of metal and semiconductor nanoparticles are important factors in catalysis, biosensing, recording media, and optical devices.

Many templates, such as DNA, peptides, polymers or surfactants, dyes, and multidentate thioethers, have been used to control the growth and assembly of nanoparticles. These templates have received attention because they adsorb on the particle surface, preventing particle aggregation, and they change the surface properties of the resulting nanostructures, allowing for careful manipulation and assembly of the nanoparticles.

These current methods used to assemble nanoparticles, however, suffer from one or more of the following shortcomings: (A) they offer no control over the shape and/or the size of the nanoparticle assembly; (B) they require multiple time-consuming synthetic steps; and (C) they are extremely low-yielding.

Assembling nanoparticles into hierarchical materials therefore remains a considerable challenge. Simple processes are needed that can be employed to assemble nanoparticles into pre-designed functional materials. Without such processes, rational incorporation of nanoparticles into new materials remains largely infeasible.

SUMMARY OF THE INVENTION

Accordingly, the present invention provides a novel strategy for controlling the formation and assembly of discrete gold nanoparticles. This strategy involves three stages: (1) providing peptide conjugates of a biomineralization peptide with a pendant organic group that conveys a self-assembly property to the conjugate; and then effecting (2) self-assembly of the peptide conjugates and (3) nucleation of nanoparticles by the conjugate assemblies. The latter two stages are accomplished concurrently; that is, in a "one pot" reaction.

In accordance with one aspect of the present invention, therefore, a conjugate molecule is provided that comprises a biomineralization peptide attached chemically at its N-terminus to a self-associating moiety. An illustrative self-associating moiety in this regard is a linear aliphatic carbon chain, and the biomineralization peptide, in one embodiment of the invention, comprises the amino acid sequence AYS-SGAPPMPPF (SEQ ID NO: 1).

According to another of its aspect, the present invention provides a plurality of conjugate molecules as described above, which plurality, when contacted with a mineralization agent, forms assemblies that template nucleation of nanoparticles comprised of a metal or semiconductor element from the mineralization agent. By the same token, the invention relates to a method for producing discrete assemblies of nanoparticles, comprising (a) providing such a plurality of conjugate molecules and then (b) contacting the plurality with a mineralization agent under conditions such that, in a single reaction mixture, self-assembly of the peptide conjugates occurs and nucleation of nanoparticles is effected by the conjugate assemblies.

Pursuant to the invention, assemblies of nanoparticles can be designed rationally and readily synthesized. In particular, the invention allows one to control the size and shape of such assemblies at will, and the entire synthetic process occurs in a single, high-yielding step.

BRIEF DESCRIPTION OF THE DRAWINGS

FIGS. 1A-1C are a schematic representation of how discrete assemblies of gold nanoparticles can be produced in accordance with the invention. FIG. 1A discloses SEQ ID NO: 1.

FIGS. 2A-2E depict data, obtained via transmission electron microscopy or tapping-mode atomic force microscopy, that illuminate $C_{12}$-$PEP_{Au}$ fiber characterization and a model of assembly, respectively. TEM images revealed that $C_{12}$-$PEP_{Au}$ amphiphiles assemble into uniform fibers (width=6.1±0.6 nm; based on 60 counts) in HEPES buffer solutions (A). These fibers had twisted-ribbon morphologies, as evidenced by tapping-mode AFM height images (B,C). The twisted nanoribbons had a regular pitch of 84.1±4.2 nm, as determined by AFM height images (based on 60 counts) (D). $C_{12}$-$PEP_{Au}$ units assembled into left-handed twisted nanoribbons (E).

DETAILED DESCRIPTION OF THE PREFERRED EMBODIMENTS

Figure 3B:
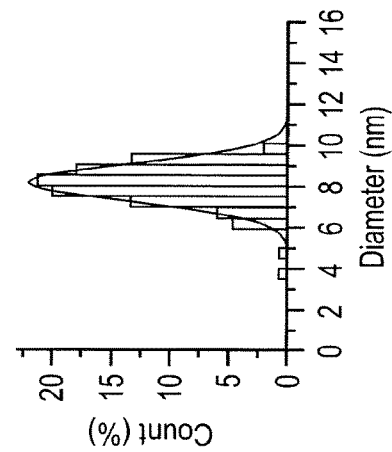
FIGS. 3A-3E present pictorial and graphical illustration of transmission electron microscopic characterization of gold nanoparticle double-helices manufactured according to the invention. Structurally regular gold nanoparticle double-helices form when a solution of chloroauric acid was added to HEPES buffer solutions containing $C_{12}$-$PEP_{Au}$, as evidenced by TEM analysis (A-D). The sizes of the gold nanoparticles are uniform 8.2±1.0 nm; based on 150 counts) (E).
Figure 3A:
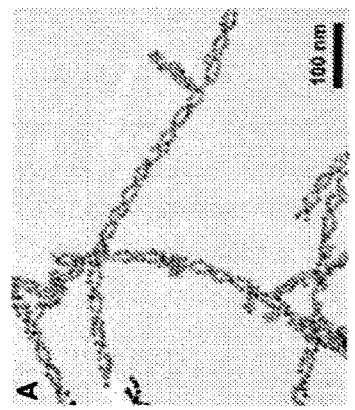
Figure 3E:
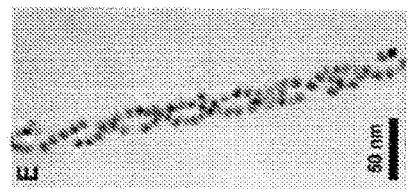
Figure 3D:
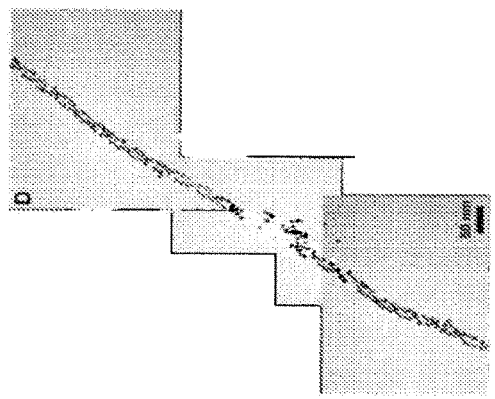
Figure 3C:
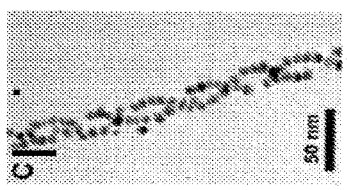

In biological systems, peptides often control the nucleation and assembly of inorganic species. Several studies have demonstrated that so-called "biomineralization peptides" can be used to bind inorganic surfaces selectively and to template the growth and nucleation of metallic nanoparticles under mild synthetic conditions. See, e.g., Naik et al., *Nature Materials* 1: 169-72 (2002); Whaley et al., *Nature* 405: 665-68 (2000); Brown, *Nature Biotechnol.* 15: 269-72 (1997). Additionally, it has been shown that peptides can be conjugated to simple organic molecules. Depending on the identity of the organic molecule, such conjugates can self-assemble to form nanofibers, nanotubules, nanovesicles, and the like. For instance, see Hartgerink et al., *Science,* 23: 1684 (2001); Jun et al., *Soft Matter* 2: 177 (2006); Zhao & Zhang, *Chem. Soc. Rev.* 35: 1105 (2006); Gazit, *Chem. Soc. Rev.* 36: 1263 (2007).

Exploiting the aforementioned self-assembly function, the present invention provides an approach, realized in a single synthetic/process step, for synthesizing and assembling nanoparticles into discrete, size-tunable, pre-designed architectures. Pursuant to this approach, a peptide conjugate is provided that comprises a biomineralization peptide chemically attached to a self-associating moiety. A plurality of such peptide conjugates d are contacted with a mineralization agent, which is typically the salt of a metal or semiconductor element, under conditions such that, in a single reaction mixture, the peptide conjugates form an assembly and the assembly nucleates nanoparticles comprised of the metal or semiconductor from the mineralization agent.

By way of example, as discussed in greater detail below, hydrophobic, linear aliphatic carbon chains, such as C10, C11, C12, C16, or C20, can be chemically attached to the N-terminus of a hydrophilic biomineralization peptide, amino acid sequence AYSSGAPPMPPF (SEQ ID NO: 1), which nucleates the formation of gold nanoparticles specifically. See Slocik et al., *Small* 1: 1048-52 (2005). The resultant amphiphilic peptide conjugate self-assembles into micelles in aqueous solution, and this micelle assembly serves both (i) to nucleate discrete gold nanoparticles and (ii) to organize the discrete gold nanoparticles spontaneously into well-defined clusters of nanoparticles (see FIG. 1).

Thus illustrated, the invention exploits the above-described amphiphilic peptides to nucleate discrete nanoparticles and, at the same time, to control their assembly into discrete clusters or infinite chains of nanoparticles. Varying the length of the aliphatic carbon chain allows for systematic adjustment of both the size of such nanoparticle clusters, typically in the range of about 30 to about 100 nm, and the shape of the clusters, either spherical or tubular.

Pursuant to this approach, the present invention more generally provides for the fabrication of nanoparticles by means of biomineralization peptides that have been engineered to nucleate specifically the formation of nanoparticles of a prescribed metallic constituency. For example, when the aforementioned amphiphilic peptide conjugate is incubated in a buffer solution containing gold salts, as further discussed below, the peptide component reduces the Au(III) salts to Au(0), thereby promoting the formation of discrete gold nanoparticles.

Chemically attaching hydrophobic organic groups, e.g., C10, C11, C12, C16, or C20 linear aliphatic carbon chains, to the N-terminus of the peptide allows for controlling the assembly of the amphiphilic peptide complex in aqueous solutions. That is, the amphiphilic peptide conjugate assembles in aqueous solution into micelles, the size and shape of which can be controlled, pursuant to the invention, by varying the length of the aliphatic carbon "tether" attached to the peptide terminus. Some tethers also are expected to result in the formation tubular micelles. See Vauthey et al., *Proc. Nat'l Acad. Sci. USA* 99: 5355 (2002); Shimizu et al., *Chem. Rev.* 105: 1401 (2005).

In any event, the peptide amphiphile micelles have hydrophobic cores (aliphatic carbon chains) and hydrophilic surfaces (peptides). The resultant spherical or tubular assemblies therefore have biomineralization peptides on their surfaces. Consequently, exposing these assemblies to solutions of selected metal salt precursors results in the nucleation of nanoparticles on the surface of the assembly. In this way, the peptide amphiphile assemblies afford control of both the growth and the assembly of nanoparticles.

The gold-reducing peptide described above is emblematic of the expanding class of biomineralization peptides, any one or more of which can be used in the present invention. Thus, bacterial and phage display technologies, see respectively Brown (1997) and Whaley et al. (2000), supra, are available for production of substrate-specific peptides that are suitable biomineralization agents for the directed nucleation that is an important aspect of the present invention. Such biomineralization peptides have been developed for producing not only of gold nanoparticles, as described above, but also of iron oxide, silica, silver, zinc sulfide, cadmium sulfide, and cobalt nanoparticles. For example, see Naik et al. (2004), supra, and Mao et al., *Proc. Nat'l Acad. Sci. USA* 100: 6946-51 (2003). Table 1 enumerates exemplary peptide sequences that exhibit affinity for various inorganics.

TABLE 1

Examples of peptide sequences exhibiting affinity for various inorganics

| Materials | Sequences | Size | pI[a] | MW[b] | Charge[c] | Display[Ref] |
|---|---|---|---|---|---|---|
| Au | MHGKTQATSGTIQS (SEQ ID NO: 2) | 14 | 8.52 | 1446.60 | +1 | CSD[1,2] |
|  | SKTSLGQSGASLQGSEKLTNG (SEQ ID NO: 3) | 21 | 8.31 | 2050.21 | +1 |  |
|  | QATSEKLVRGMEGASLHPAKT (SEQ ID NO: 4) | 21 | 8.60 | 2211.52 | +1 |  |
| Pt | DRTSTWR (SEQ ID NO: 5) | 7 | 9.60 | 920.98 | +1 | PD[d] |
|  | QSVTSTK (SEQ ID NO: 6) | 7 | 8.75 | 749.82 | +1 |  |
|  | SSSHLNK (SEQ ID NO: 7) | 7 | 8.49 | 771.33 | +1 |  |
| Pd | SVTQNKY (SEQ ID NO: 8) | 7 | 8.31 | 838.92 | +1 | PD[d] |
|  | SPHPGPY (SEQ ID NO: 9) | 7 | 6.46 | 753.81 | 0 |  |
|  | HAPTPML (SEQ ID NO: 10) | 7 | 6.74 | 765.93 | 0 |  |

TABLE 1-continued

Examples of peptide sequences exhibiting affinity for various inorganics

| Materials | Sequences | Size | pI[a] | MW[b] | Charge[c] | Display[Ref] |
|---|---|---|---|---|---|---|
| Ag | AYSSGAPPMPPF[e] (SEQ ID NO: 11) | 12 | 5.57 | 1221.39 | 0 | PD[3] |
|  | NPSSLFRYLPSD[e] (SEQ ID NO: 12) | 12 | 6.09 | 1395.53 | 0 |  |
|  | SLATQPPRTPPV[e] (SEQ ID NO: 13) | 12 | 9.47 | 1263.46 | +1 |  |
| $SiO_2$ | MSPHPHPRHHHT[e] (SEQ ID NO: 14) | 12 | 9.59 | 1470.63 | +1 | PD[4] |
|  | RGRRRRLSCRRL[e] (SEQ ID NO: 15) | 12 | 12.30 | 1541.89 | +6 |  |
|  | KPSHHHHHTGAN (SEQ ID NO: 16) | 12 | 8.78 | 1359.43 | +1 |  |
| Zeolites | VKTQATSREEPPRLPSKHRPG (SEQ ID NO: 17) | 21 | 10.90 | 2371.68 | +3 | CSD[5] |
|  | MDHGKYRQKQATPG (SEQ ID NO: 18) | 14 | 9.70 | 1616.82 | +2 |  |
| ZnO | NTRMTARQHRSANHKSTQRA[e] (SEQ ID NO: 19) | 20 | 12.48 | 2351.59 | +4 | CSD[6] |
|  | YDSRSMRPH (SEQ ID NO: 20) | 0 | 8.75 | 1148.26 | +1 |  |
| $CaCO_3$ | HTQNMRMYEPWF (SEQ ID NO: 21) | 12 | 6.75 | 1639.87 | 0 | PD[7] |
|  | DVFSSFNLKHMR (SEQ ID NO: 22) | 12 | 8.75 | 1480.70 | +1 |  |
| $Cr_2O_3$ | VVRPKAATN (SEQ ID NO: 23) | 9 | 11.00 | 955.13 | +2 | CSD[5] |
|  | RIRHRLVGQ (SEQ ID NO: 24) | 9 | 12.30 | 1134.35 | +3 |  |
| $Fe_2O_3$ | RRTVHKKVN[e] (SEQ ID NO: 25) | 9 | 12.01 | 1146.32 | +3 | CSD[8] |
| GaAs | AQNPSDNNTHTH (SEQ ID NO: 26) | 12 | 5.97 | 1335.31 | 0 | PD[9] |
|  | RLELAIPLQGSG (SEQ ID NO: 27) | 12 | 6.00 | 1253.46 | 0 |  |
|  | TPPRPIQYNHTS (SEQ ID NO: 28) | 12 | 8.44 | 1410.55 | +1 |  |
| ZnS | NNPMHQN[e] (SEQ ID NO: 29) | 7 | 6.74 | 853.91 | 0 | PD[10] |

[a]Isoelectric points and [b]Molecular masses of peptides calculated using Compute pI/Mw tool (http://us.expasy.org/tools/pi_tool.html).
[c]Calculated by subtracting the number of basic residues (R and K) from the number acidic residues (D and E).
[d]Unpublished results by Sarikaya et al., Nature Materials 2: 577-85 (2003).
[e]Most frequently observed sequences.
[1]Brown, Nature Biotechnol. 15: 269-72 (1997).
[2]Brown et al., J. Mol. Biol. 299: 725-32 (2000).
[3]Naik et al., Nature Materials 1: 169-72 (2002).
[4]Naik et al., J. Nanosci. Nanotechnol. 2: 1-6 (2002).
[5]Scembri et al., FEMS Microbiol. Lett. 170: 363-71 (1999).
[6]Kiargaard et al., Appl. Env. Microbiol. 66: 10-14 (2000).
[7]Gaskin et al., Biotech. Lett. 22: 1211-16 (2000).
[8]Brown et al., Proc. Nat'l Acad. Sci. USA 89: 8651-55 (1992).
[9]Whaley et al., Nature 405: 665-68 (2000).
[10]Lee et al., Science 296: 892-95 (2002).

In addition, multifunctional peptides that form bimetallic nanostructures, see Slocik & Naik, *Advanced Materials* 18: 1988-92 (2006), are available for use in accordance with the present invention. Accordingly, the invention contemplates production of nanoparticle assemblies that comprise more than one metallic or semiconductor constituent, through the use of biomineralization peptides of differing specificity or biomineralization peptides that are multifunctional. Further in this vein, two separate biomineralization peptides could be coupled together by an organic moiety that serves to both assemble and crosslink the two peptides.

The above-mentioned aliphatic carbon tails likewise are illustrative of the pendant organic group that can be attached to the terminus of a biomineralization peptide, according to the present invention, thereby to effect assembly of supra-molecular structures, exemplified below by micellar and tubular amphiphilic structures. Pursuant to the invention, any such supramolecular assembly can be employed as a template for the simultaneous nucleation and assembly of nanoparticles, as described above.

It also is feasible, pursuant to the invention, to control the spacing between nanoparticles that comprise an assembly, as described above, by adding a charged particle-stabilizing ligand during the assembly process. Such a ligand forces the constituent particles apart, in effect allowing one to adjust inter-particle spacing by adjusting the amount of citrate or other ligand that is added to the synthesis. Illustrative of the category of suitable stabilizing ligands in this context those chosen from the organic and inorganic molecules identified as "surface stabilizers" in the field of nanoparticulate pharmaceutical formulations. See published U.S. application 2008/0220075, the relevant contents of which (see paragraphs 0087-0107) are incorporated herein by reference. Among these are various polymers, low molecular-weight oligomers, natural products, and surfactants, including non-ionic, cationic, zwitterionic, and ionic surfactants. Preferred stabilizing ligands are citrate, bis(p-sulphonatophenyl)phenylphosphine dihydrate dipotassium, and ascorbate.

In addition to variation of the biomineralization peptide, thereby to program the composition of the nanoparticle assembly, the present invention thus further encompasses the use of a variety of pendant organic groups or "self-associating moieties" that can be attached to the peptide, in order to control supramolecular assembly. The following are illustrative of this category of self-associating moieties:
(1) "Superhydrophobic" fluorous organic groups, such as perfluorocarbon moieties, display intense hydrophobic and lipophobic effects, which provide a powerful non-covalent, labile binding interaction that can promote selective self-assembly in solvents of varying polarity. See, e.g., Martin & Mecozzi, *Supramolecular Chem.* 17: 9-15 (2005).
(2) Aromatic and π-conjugated organic groups are characterized by self-assembly that is effected and controlled via π-stacking interaction, caused by intermolecular overlapping of p-orbitals in π-conjugated systems. See, e.g., Brunsveld et al., *Proc. Nat'l Acad. Sci. USA* 99: 4977-82 (2002). A variation on this theme would be organics with both π-stacking motifs (e.g., large aromatic ring systems) and aliphatic portions.
(3) Amphiphilic organic molecules have both hydrophilic and hydrophobic portions, which foster interactions that promote self-assembly. See, e.g., Yamamoto et al., *Science* 314: 1761 (2006); Percec et al., *Nature* 430: 764 (2004).
(4) Organic molecules with metal-binding motifs, when attached to biomineralization peptides, allow for the use of simple coordination chemistry to direct the assembly of the peptides into predetermined structures not otherwise accessible by using only organic groups. See, e.g., Sever et al., *Angew. Chem. Int. Ed.* 43: 448 (2004); Sever & Wilker, *Tetrahedron* 57: 6139 (2001).
(5) Other peptides that assemble into beta-sheet structures, such as a peptide with the amino acid sequence FKFEFKFE (SEQ ID NO: 30), see Matsuura et al., *J. Am. Chem. Soc.* 127: 10148 (2005), can be attached to biomineralization peptides of the invention, in order to take advantage of the secondary bioassembly afforded by the beta-sheet peptide, thereby to organize the nucleation conjugates. See, e.g., Dong et al., *J. Am. Chem. Soc.* 129: 12468 (2007).
(6) Oligonucleotides can be attached to biomineralization peptides, permitting one to program the assembly of the resultant peptide conjugates by controlling the length and sequence of the oligonucleotides moiety. For example, see Marchán et al., *Eur. J. Org. Chem.* 2000, 2495; Stetsenko & Gait, *J. Org. Chem.* 65: 4900 (2000); Wang et al., *Bioconjugate Chem.* 16: 497 (2005).
(7) Two or more biomineralization peptides, either the same or different, can be crosslinked, using organic groups that have multiple peptide-attachment sites. In such cases, the organic moiety can serve not only to crosslink the peptides but also to effect their assembly into supramolecular systems. This expediency allows for incorporating two or more different biomineralization peptides into the same material, yielding structures comprised of nanoparticles of varying composition.

Chemistries are well-known for attaching such pendant organic groups to the N-termini of biomineralization peptides according to the invention. See Hermanson, Greg T., BIOCONJUGATE TECHNIQUES, Pierce Chemical Company (Rockford, Ill.). In general, the organic group should have one or more carboxylic acid functional groups, which can be derivatized with succinimide groups. Succinimide groups react selectively with primary amines, such as those found at the N-termini of peptides as described here, to produce an amide bond.

The present invention is further described by reference to the following examples, which are illustrative only.

Example 1

Fabrication of Discrete, Sub-50 nm Gold Nanoparticle Assemblies

Reagents and solvents were obtained from commercial sources and used without further purification. Reversed-phase HPLC was performed at ambient temperature with Agilent 1200 liquid chromatograph, equipped with diode array and multiple wavelength detectors using a Grace Vydac protein C4 column. MALDI-TOF mass spectra were obtained on a PE Applied Biosystem Voyager System 1180 spectrometer, with α-cyano-4-hydroxy cinnamic acid (CHCA) as matrix. TEM samples were prepared by pipetting one drop of solution onto a 3-mm-diameter copper grid coated with carbon film. Transmission electron microscopy (TEM) was conducted on a JEOL 200F instrument operated at 200 kV. Dynamic light scattering (DLS) was measured at 22° C. with a Brookhaven 90Plus Particle Size Analyzer.

For the preparation of the N-hydroxyl-succinimide esters, the related carboxylic acid and one equivalent N-hydroxy-succinimide were dissolved in dry DMF solution in an argon atmosphere. After addition of 1.1 equivalent of dicyclohexyl carbodiimide (DCC) at 0° C., the solution was stirred overnight at room temperature. The precipitate solid was filtered off, and the clear filtrated solution was then evaporated to dryness and used directly from next step reaction without further purification.

To prepare the conjugated peptide, peptide with sequence of AYSSGAPPMPPF (SEQ ID NO: 1) (1.26 mg, $1.03*10^{-6}$ mol), see Slocik et al. (2005), supra, was dissolved in 0.1 mL dry DMF. After addition of about three equivalents of related N-hydroxyl-succinimide ester and 1 μL Et3N under stirring, the solution was stirred at room temperature for a few hours. The pure conjugated peptide was obtained by running reversed-phase HPLC eluting with a linear gradient of $CH_3CN$ containing 0.05% formic acid/water containing 0.1% formic acid (5/95 to 95/5 over 30 minutes; isolated yield: 92.28%)

The synthesis of the peptide-Au nanoparticle was carried out by mixing the conjugated peptide, HEPES buffer and aqueous chloroauric acid (HAuCl$_4$) solution, the formation of gold nanoparticles was indicated by the appearance of color of the above mixed solution, which can also be seen from their UV/Vis spectra. Confirmation of discrete nanoparticle cluster formation was confirmed by TEM.

To verify that the micelle was templating the formation of the gold nanoclusters, the inventors endeavored to perform the identical synthesis at 60° C. Such procedures resulted in the formation of discrete nanoparticles, which showed some degree of random aggregation. This result was expected, as the micelle should not be thermodynamically stable at such elevated temperatures.

Finally, the inventors also attempted to synthesize the gold nanoclusters by incubating the C12-peptide conjugate in pH 7.5 HEPES buffer with small additions of CH$_3$CN, an organic solvent expected to disrupt the formation of the micelle, discrete, irregularly-shaped nanoparticles formed, upon addition of HAuCl$_4$. No nanoclusters were observed.

The inventors thus exemplified their novel strategy for synthesizing pre-designed nanoclusters, around 44 nm in size, by using micelles constructed from amphiphilic organic-peptide conjugates. Exposing these constructs to gold salts results in the nucleation of gold nanoparticles on the surface of the micelle. This illustrates how the inventive strategy allows for the simultaneous nucleation and assembly of nanoparticles.

Example 2

Construction of Highly-Ordered Gold Nanoparticle Double-Helices

The inventors attached small organic molecules to the peptide mentioned in Example, AYSSGAPPMPPF (SEQ ID NO: 1) (hereafter "PEP$_{Au}$"), and then they investigated the assembly of the resultant peptide conjugates. PEP$_{Au}$ was evolved and isolated, to have a high affinity for gold surfaces, via phage-display methodology as described, for example, by Slocik et al., *Small* 1: 1048-52 (2005). Given the hydrophilic nature of PEP$_{Au}$, attaching an aliphatic carbon tail to its N-terminus was expected to promote its assembly into various multi-dimensional supramolecular assemblies, such as a 1-D peptide amphiphile structure.

As a first step in this direction, the inventors coupled succinimide-activated dodecanoic acid to the N-terminus of PEP$_{Au}$ to generate [C$_{11}$H$_{23}$CO]-PEP$_{Au}$ (C$_{12}$-PEP$_{Au}$). The latter was completely dissolved in 0.1 M HEPES buffer, which allowed for both C$_{12}$-PEP$_{Au}$ self-assembly and gold nanoparticle nucleation. The structure of the resultant peptide-amphiphile assembly was examined by means of transmission electron microscopy (TEM) and tapping-mode atomic force microscopy (AFM). TEM images (FIG. 2a) revealed the presence of uniform individual fibers with micrometer lengths (>4 µm) and narrow (6.1±0.6 nm) widths. Tapping-mode AFM showed that each fiber adopted a twisted-ribbon morphology and that the ribbons appeared to twist in a left-handed direction (FIG. 2b). The pitch of the twisted-nanoribbon was consistently measured to be 84.1±4.2 nm (FIG. 2c).

Spectroscopic studies were performed to clarify the structure of the helical fibers. Specifically, the inventors examined the fibers via circular dichroism spectroscopy, and they observed a peak around 227 nm, which could correspond to the signal produced by β-sheet structures. To probe whether β-sheet formation occurs, the assembled species were analyzed using fourier transform infrared (FT-IR) spectroscopy. The peak at 3275 cm$^{-1}$ corresponded to the stretching frequency of hydrogen-bonded N—H groups. The amide I band (1626 cm$^{-1}$) was consistent with β-sheet conformations, and the C—H vibration bands at 2918 cm$^{-1}$ and 2850 cm$^{-1}$ indicate ordered packing of the aliphatic chains.

With these spectroscopic and microscopy data, the inventors arrived at a working model for the resultant structure of the nanoribbon assembly (FIG. 2e). The width of the nanoribbon is spanned by two C$_{12}$-PEP$_{Au}$ units that interact through their aliphatic tails. Organization of the C$_{12}$-PEP$_{Au}$ units along the longitudinal axis of the nanoribbon is driven by the formation of parallel β-sheets and favorable hydrophobic interactions between the aliphatic tails. The first four amino acids (AYSS (SEQ ID NO: 31)) have a propensity to form β-sheets, whereas proline residues do not. See Mino et al., *Nature* 367: 660-63 (1994). Accordingly, these amino acids (AYSS (SEQ ID NO: 31)) were understood to participate in β-sheet assembly and also to impart the left-handed helical twist to the nanoribbon.

The formation of nanoribbons can be attributed to the fact that the outer two-thirds of the peptide sequence is relatively sterically bulky, due to the presence of two proline-proline dimers and one phenylalanine. The steric bulk causes the C$_{12}$-PEP$_{Au}$ units to assemble into nanoribbon structures rather than condensed tubular micelles, while at the same time PEP$_{Au}$ subunits effectively shield the hydrophobic core of the nanoribbon.

The inventors sought to determine whether this process of peptide self-assembly and the process of PEP$_{Au}$ biomineralization could be coupled into a single, unified process, facilitating the design and construction of double-helical gold nanoparticle superstructures. To this end, solutions of chloroauric acid (HAuCl$_4$) were added to clear HEPES buffer solutions containing C$_{12}$-PEP$_{Au}$, which were carefully filtered to remove any assembled structures. Immediately after the addition of HAuCl$_4$, TEM samples were prepared and their examination revealed that the C$_{12}$-PEP$_{Au}$ fibers formed even in the presence of the gold salt.

When the solutions were allowed to stand for ~30 minutes, a small amount of precipitate formed. TEM studies of the precipitate indicated formation of double-helical assemblies comprising uniform discrete spherical gold nanoparticles (FIG. 3a-e).

A better understanding of the structure of the nanoparticle assemblies was obtained from electron tomographic analysis. A series of tilted images from −70° to +70° with 1° tilt intervals were collected. These tilted projections were aligned and combined computationally to reconstruct a three-dimensional electron density map (tomogram).

Figure 4B:
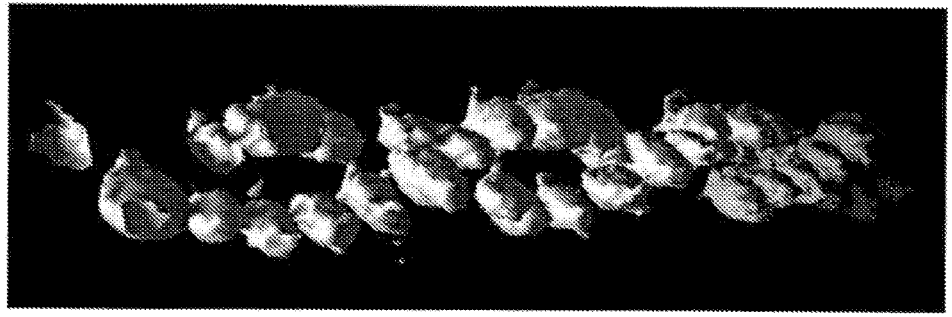
FIGS. 4A-4C provide electron tomography data (A,B) and schematic depiction of the formation of gold nanoparticle double-helices manufactured according to the invention (C). The structure of a gold nanoparticle double-helix was confirmed using electron tomography. X-Y computational slices (a, I-VIII) of the 3-D tomographic volume containing the double-helical gold nanoparticle assembly and a 3-D surface rendering of the tomographic volume (B) both revealed the left-handed nature of the helices. Left-handed gold nanoparticle double-helices were synthesized and assembled directly in a reaction containing HEPES buffer solutions of chloroauric acid and $C_{12}$-$PEP_{Au}$ (C).
Figure 4A:
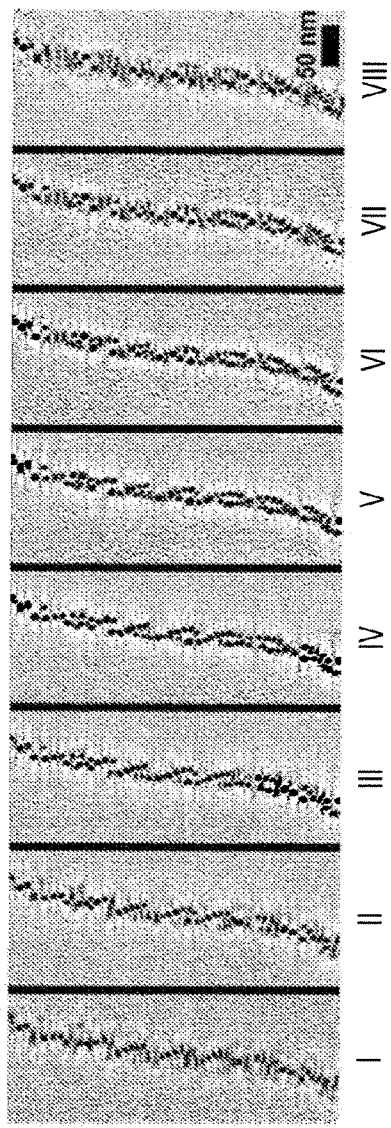

As illustrated in the tomographic slices (FIG. 4a) and in a 3-D surface rendering of the reconstructed density map (FIG. 4b), the gold nanoparticle assemblies are left-handed double-helices, which comports with the observed chirality of the twisted C$_{12}$-PEP$_{Au}$ nanoribbons. The measured maximum inner-distance between the particles along the width of the double-helix is 6.0±0.8 nm, and the pitch of the double-helix is 83.2±4.4 nm. Both distances are consistent with the observed width and pitch of the twisted C$_{12}$-PEP$_{Au}$ nanoribbons.

Figure 4C:
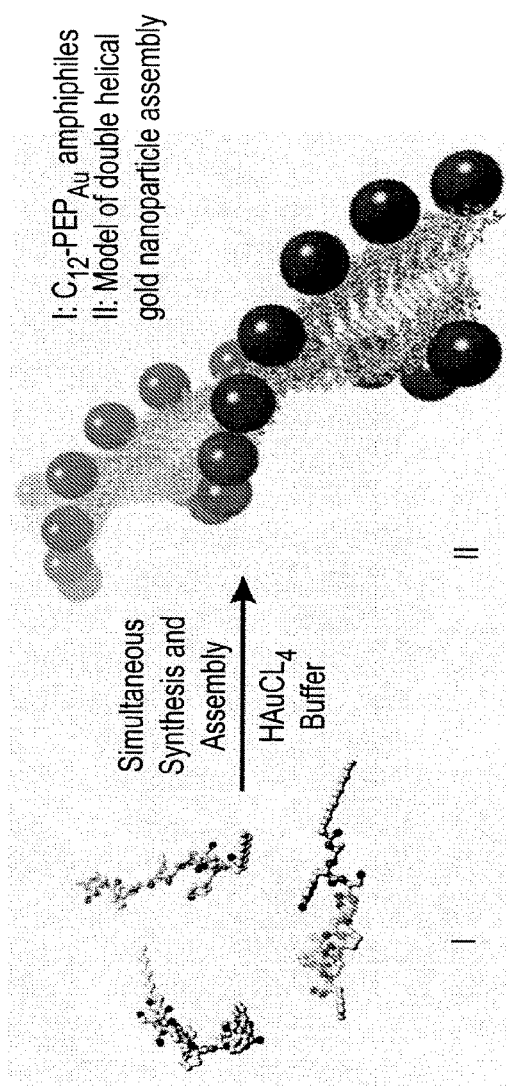

These observations indicate that the synthesis of the nanoparticles and the assembly of the nanoribbons were coupled and that the peptide-conjugates of the invention successfully controlled the formation of gold nanoparticle double helices (FIG. 4c). The results of control experiments help verify this conclusion. That is, when identical syntheses were performed using unmodified PEP$_{Au}$ instead of C$_{12}$-PEP$_{Au}$, dispersed nanoparticles formed that were similar to those reported by Slocik et al. (2005), supra.

To assess the importance of the internal amino acids (AYSS (SEQ ID NO: 31)) for directing the assembly of the nanoribbons, see Paramonov et al., *J. Am. Chem. Soc.* 128: 7291-98 (2006), the inventors attempted to assemble nanoribbons and to synthesize the gold nanoparticle double-helices, using an amphiphile constructed from the reverse peptide sequence ($C_{12}$-FPPMPPAGSSYA (SEQ ID NO: 32)). Nanoribbons did not form with this amphiphile, nor did gold nanoparticle double-helices; rather, random gold aggregates were the principle product. Finally, to determine whether the $C_{12}$-PEP$_{Au}$ nanoribbons could template the assembly of pre-formed gold nanoparticles, the inventors added citrate-stabilized nanoparticles to HEPES solutions containing $C_{12}$-PEP$_{Au}$ nanoribbons. In this case, no ordered particle assemblies were observed.

The formation of left-handed gold nanoparticle double-helices in a single preparative step underscores the utility and power of the inventive methodology. The gold nanoparticles comprising the double helices are monodisperse, with diameters of 8.2±1.0 nm (FIG. 3*e*), which indicates a uniform growth process from initial seeding to termination. In addition, the double-helices are highly regular: there are approximately 22 nanoparticles per pitch distance, the edge-to-edge spacing between the nanoparticles is uniform (1.5±0.8 nm), and the length of individual helices extends into the micrometer range. Such structural uniformity is unique, and it will be important for many applications, especially those that derive from the plasmonic properties of the nanoparticles.

In addition, spatially complex nanoparticle superstructures are very rare that exhibit well-defined stereochemistry, order, and persistence over multiple length scales, and rational synthetic methodology that allows for their fabrication is equally scarce. Having achieved this with the present invention means that the targeting of various nanoparticle superstructures is feasible, pursuant to the invention, via variation of the pendant organic group and by tuning the inorganic composition of the assemblies via selection of particular peptides. Thus, the invention can be useful for designing and producing many other target nanoparticle superstructures, characterized by properties that depend both on the composition of the organic and inorganic components and on their arrangement with respect to one another within the assembled structure.

What is claimed is:

1. A nanostructure comprising: (a) a conjugate molecule comprising a biomineralization peptide attached chemically at its N-terminus to a self-associating moiety, wherein the self-associating moiety is selected from a linear aliphatic carbon chain and an aromatic organic group; and (b) a nanoparticle comprising a metal or semiconductor element; wherein the biomineralization peptide binds to the metal or semiconductor element of the nanoparticle.

2. The nanostructure according to claim 1, wherein the self-associating moiety is a linear aliphatic carbon chain.

3. The nanostructure according to claim 1, wherein the self-associating moiety comprises succinimide-activated dodecanoic acid.

4. The nanostructure according to claim 1, wherein the biomineralization peptide comprises the amino acid sequence AYSSGAPPMPPF (SEQ ID NO: 1).

5. The nanostructure according to claim 1, wherein the self-associating moiety is a linear aliphatic carbon chain.

6. The nanostructure according to claim 1, wherein the self-associating moiety is an aromatic organic group.

7. The nanostructure according to claim 1, wherein the biomineralization peptide exhibits an affinity for nanoparticles comprising gold, iron oxide, silica, silver, zinc sulfide, cadmium sulfide, or cobalt.

8. The nanostructure according to claim 7, wherein the biomineralization peptide exhibits an affinity for nanoparticles comprising cobalt.

9. The nanostructure according to claim 7, wherein the biomineralization peptide exhibits an affinity for nanoparticles comprising gold.

* * * * *